United States Patent
Dunn et al.

(10) Patent No.: US 10,150,817 B2
(45) Date of Patent: Dec. 11, 2018

(54) RAPID GENERATION OF ANTI-IDIOTYPIC ANTIBODIES

(75) Inventors: Robert J. Dunn, San Diego, CA (US); Marilyn R. Kehry, San Diego, CA (US)

(73) Assignee: Biogen MA Inc., Cambridge, MA (US)

( * ) Notice: Subject to any disclaimer, the term of this patent is extended or adjusted under 35 U.S.C. 154(b) by 1209 days.

(21) Appl. No.: 13/820,229

(22) PCT Filed: Aug. 31, 2011

(86) PCT No.: PCT/US2011/050001
§ 371 (c)(1),
(2), (4) Date: Aug. 12, 2013

(87) PCT Pub. No.: WO2012/030982
PCT Pub. Date: Mar. 8, 2012

(65) Prior Publication Data
US 2013/0330323 A1    Dec. 12, 2013

Related U.S. Application Data

(60) Provisional application No. 61/379,089, filed on Sep. 1, 2010.

(51) Int. Cl.
C07K 16/42    (2006.01)
C07K 16/28    (2006.01)

(52) U.S. Cl.
CPC ...... C07K 16/4258 (2013.01); C07K 16/2887 (2013.01); C07K 16/4208 (2013.01); C07K 2317/52 (2013.01)

(58) Field of Classification Search
None
See application file for complete search history.

(56) References Cited

U.S. PATENT DOCUMENTS

| | | |
|---|---|---|
| 2002/0102264 A1 | 8/2002 | Cheung |
| 2003/0072762 A1 | 4/2003 | van de Winkel et al. |
| 2007/0136826 A1 | 6/2007 | Dunn et al. |

FOREIGN PATENT DOCUMENTS

| | | |
|---|---|---|
| EP | 0 306 995 A2 | 3/1989 |
| EP | 0 498 767 A2 | 8/1992 |
| EP | 0 502 416 B1 | 12/1997 |
| WO | WO 93/24647 A1 | 12/1993 |

OTHER PUBLICATIONS

Beare et al., "The CD System of Leukocyte Surface Molecules Monoclonal Antibodies to Human Cell Surface Antigens", Curr. Protoc. Immunol. 80:A.4A.1-A.4A.73, 2008.*
Bekar, K.W., et al., "Prolonged Effects of Short-Term Anti-CD20 B Cell Depletion Therapy in Murine Systemic Lupus Erythematosus," *Arthritis & Rheumatism* 62(8):2443-2457, American College of Rheumatology, United States (2010).
Cragg, M.S., et al., "A new anti-idiotype antibody capable of binding rituximab on the surface of lymphoma cells," *Blood* 104:2540-2542, The American Society of Hematology, United States (2004).
Czuczman, M.S., et al., "Treatment of Patients With Low-Grade B-Cell Lymphoma With the Combination of Chimeric Anti-CD20 Monoclonal Antibody and CHOP Chemotherapy," *J Clin Oncol* 17:268-276, American Society of Clinical Oncology, United States (1999).
Field, S.K. and Morrison, D.C., "An Anti-Idiotype Antibody Which Mimics the Inner-Core Region of Lipopolysaccharide Protects Mice against a Lethal Challenge with Endotoxin," *Infection and Immunity* 62(9):3994-3999, American Society for Microbiology, United States (1994).
Gruber, R., et al., "The Human Antimouse Immunoglobulin Response and the Anti-idiotypic Network Have No Influence on Clinical Outcome in Patients with Minimal Residual Colorectal Cancer Treated with Monoclonal Antibody CO17-1A," *Cancer Research* 60:1921-1926, American Association for Cancer Research, United States (2000).
Hong, K., et al., "Simple quantitative live cell and anti-idiotypic antibody based ELISA for humanized antibody directed to cell surface protein CD20," *Journal of Immunological Methods* 294:189-197, Elsevier B.V., Netherlands (2004).
Levy, R. and Miller, R.A., "Therapy of Lymphoma Directed at Idiotypes," *J Natl Cancer Inst Monogr* 10:61-68, Oxford University Press, England (1990).
Liu, Z., et al., "Generation of Anti-Idiotype Antibodies for Application in Clinical Immunotherapy Laboratory Analyses," *Hybridoma and Hybridomics* 22(4):219-228, Mary Ann Liebert, Inc., United States (2003).
Rodriguez, M., et al., "Generation and Characterization of an Anti-Idiotype Monoclonal Antibody Related to GM3(NeuGc) Ganglioside," *Hybridoma and Hybridomics* 22(5):307-314, Mary Ann Liebert, Inc., United States (2003).
Yu, S., et al., "B Cell Depletion Inhibits Spontaneous Autoimmune Thyroiditis in NOD.H-2h4 Mice," *The Journal of Immunology* 180:7706-7713, The American Association of Immunologists, Inc., United States (2008).
Keler, T., et al., "Targeting Weak Antigens to CD64 Elicits Potent Humoral Responses in Human CD64 Transgenic Mice," *The Journal of Immunology* 165:6738-6742, The American Association of Immunologists, United States (2000).

\* cited by examiner

*Primary Examiner* — G. R. Ewoldt
(74) *Attorney, Agent, or Firm* — Wolf, Greenfield & Sacks, P.C.

(57) ABSTRACT

The present disclosure relates to in vivo methods for producing anti-idiotypic antibodies. In some aspects, anti-idiotypic antibodies are generated by co-administering to a mouse a first antibody having a murine IgG2a isotype and a second antibody that targets mouse B cells and has a murine IgG2a isotype. In some embodiments, the mouse expresses the Igh-$1^b$ allele of IgG2a, and the second antibody binds a mouse B cell surface marker selected from the group consisting of CD19, CD20, CD21, CD22, CD40, CD45, IgM, and IgD.

25 Claims, 11 Drawing Sheets

Figure 1:
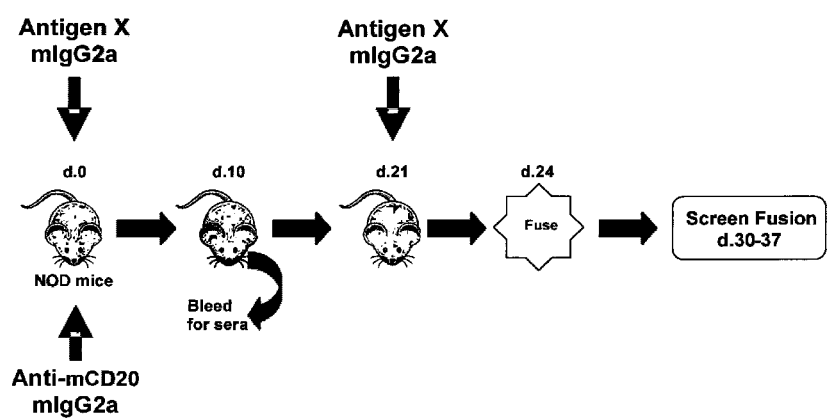

A.

B.

RAPID GENERATION OF ANTI-IDIOTYPIC ANTIBODIES

BACKGROUND OF THE INVENTION

Field of the Invention

The present invention provides methods for generating anti-idiotypic antibodies and compositions comprising the antibodies.

Background Art

Anti-idiotypic antibodies are defined as antibodies that target specific epitopes, called isotopes, on another antibody that are unique for that target antibody. The collection of isotopes for a given antibody defines its idiotype, and is generally found in the complementarity determining regions (CDRs) of the targeted antibody. Polyclonal anti-idiotypic antibodies have been used experimentally since the 1950's, but it was not until the mid-1970's that a modern theory was proposed for how self-generated anti-idiotypic antibodies might help control the immune system by regulating antibody production (Jerne, 1974). The discovery of a method for producing monoclonal antibodies a year later (Köhler and Milstein, 1975) opened the door for the creation and isolation of monoclonal anti-idiotypic antibodies that have specificity for a unique variable domain found exclusively on a specific target antibody. In support of the idiotype-anti-idiotype immune regulation theory, dosing neonatal mice with anti-idiotypic antibodies derived from perinatal B cell fusions was shown to greatly alter the B cell repertoire by possibly limiting the expression or expansion of self-reactive B cells (Kearney et al., 1989).

The utility of monoclonal anti-idiotypic antibodies has been demonstrated in a number of ways. To date, the most common usage of anti-idiotype monoclonal antibodies has been the in vitro development of pharmacokinetic enzyme-linked immunosorbant assays (ELISAs) that measure circulating sera levels of a dosed monoclonal antibody, or simply as a positive standard for measurement of anti-idiotype immune responses to therapeutic mouse (HAMA), chimeric (HACA), or human (HAHA) monoclonal antibodies (Liu et al., 2003). The specificity of an anti-idiotypic antibody allows for the detection of only the antibody of interest in the presence of endogenous polyclonal circulating antibody. Accurate quantification of circulating therapeutic antibody levels is an important and frequently challenging aspect of antibody drug development.

Another use of anti-idiotypic antibodies is the exploitation of their variable domain as a physical "internal image" of the anti-idiotype's target idiotope. The creation of a second generation anti-idiotype antibody to the first anti-idiotype antibody has the potential to target idiotopes that mimic epitopes found on the original antigen (Rodríquez et al., 2003). This can allow for the creation of new antibodies to the original antigen with subtly different binding characteristics to the same or proximal epitopes.

Along this same theme, anti-idiotypic monoclonal antibodies can be used as vaccines, especially to non-protein or potentially toxic pathogens. This has been demonstrated in vivo by immunizing mice with an anti-idiotype monoclonal to an anti-lipopolysaccharide (LPS) antibody, thereby generating circulating antibody that can bind the original LPS antigen and provide protection to the mice during a subsequent and otherwise lethal LPS challenge (Field et al., 1994). Another enterprising use of anti-idiotypic monoclonal antibodies is as a potential therapy for B cell lymphomas (Levy and Miller, 1990). Since generating anti-idiotypic antibodies has been difficult and time consuming, these efforts were not focused on providing individualized therapies, but rather by generating cross-reactive anti-idiotypic antibodies that recognized shared idiotopes of the B-cell receptors on clonally distinct lymphomas from multiple patients. Interest in this form of anti-lymphoma therapy peaked in the early 1990's and was eventually eclipsed by the success of the pan-B cell-selective anti-CD20 therapy, rituximab (Czuczman et al., 1999).

The generation of anti-idiotype serum titers in mice for monoclonal antibody generation can be challenging and requires prolonged immunizations. Immunizations of non-mouse species such as rats or hamsters with mouse antibodies frequently generate non-anti-idiotypic antibodies due to the antigenic dominance exhibited by Heavy (H) and Light (L) chain constant (C) region epitopes and result in antibodies to isotypes that may or may not be strain or even species specific. Syngeneic immunizations of mice using antibody-carrier conjugates to keyhole limpet hemocyanin (KLH) (Raychaudhuri et al., 1986) or antibody in less-favored CFA emulsions (Yakulis et al., 1972) have been successful in generating anti-idiotypic antibodies, but both approaches require multiple immunizations over the course of months.

BRIEF SUMMARY OF THE INVENTION

The present invention provides a method of preparing anti-idiotypic antibodies. In one embodiment, the invention provides a method for producing anti-idiotypic antibodies comprising: (a) co-administering to an animal a first antibody having a murine IgG2a isotype; and a second antibody that targets B cells and has a murine IgG2a isotype; wherein the first and second antibodies have different binding specificities; and (b) isolating the anti-idiotypic antibodies which specifically bind to the first antibody in step (a). In one embodiment, the animal is susceptible to autoimmune disease. In a further embodiment, the animal is a mouse.

In one embodiment, the method further comprises producing a hybridoma fusion of spleen cells from the immunized animal and myeloma fusion partners and isolating the monoclonal anti-idiotypic antibodies that specifically bind the first antibody. In a further embodiment, the myeloma fusion partners are either NS-1 or SP2/0 cells.

In one embodiment, the mouse expresses the Igh-$1^b$ allele of IgG2a. In another embodiment, the mouse is non-obese diabetic (NOD), non-obese resistant (NOR), SJL, C.B-17, or C57BL/6. In a further embodiment, the mouse is a NOD mouse.

In one embodiment of the invention, the co-administration is performed sequentially. In another embodiment, the sequential co-administrations are given as boosting administrations. In a further embodiment, the co-administration is performed simultaneously.

In one embodiment of the invention, the first and second antibody are administered at a ratio of about 1:1. In one embodiment of the invention, the first and second antibody are administered at a ratio of about 1:2. In one embodiment of the invention, the first and second antibody are administered at a ratio of about 1:4.

In one embodiment of the invention, the second antibody binds a B cell surface marker. In another embodiment, the B cell surface marker is CD19, CD20, CD21, CD22, CD40, CD45, IgM, or IgD. In yet another embodiment, the second antibody is the anti-mCD20 antibody 18B12.

In one embodiment of the invention, the first antibody specifically binds an antigen selected from the group consisting of: alpha-4-integrin, glycoprotein IIb/IIIa, vascular endothelial growth factor, epidermal growth factor, complement C5 protein, ErbB2, CD3 receptor, CD11a, CD20, CD23, CD25, CD33, CD52, BCMA, CD40, Lymphotoxin α, Lymphotoxin $α_1β_2$, LIGHT, TWEAK, CD154, VLA4, EGFR, IGF1R, CD169, IL-6, IL-23, TNF-α, Neonatal Fc Receptor (FcRn), BDCA-2, DCIR, DR6 (Death Receptor 6), LINGO-1, Tyro3, RON receptor tyrosine kinase, DDR1 (Discoidin Domain Receptor 1), HER3, FNI4, VEGF and CD103. In another embodiment, the first antibody comprises the variable domains of rituximab.

The invention also provides an anti-idiotypic antibody produced by the methods described herein.

In one embodiment, the invention provides a pharmaceutical composition comprising an anti-idiotypic antibody of the invention and a pharmaceutically acceptable diluent, carrier, salt or adjuvant.

In one embodiment, the present invention provides a method of decreasing the half-life of a therapeutic antibody in a subject comprising administering an effective amount of an anti-idiotypic antibody of the invention to the subject, wherein the anti-idiotypic antibody specifically binds the therapeutic antibody. In one embodiment, the present invention provides a method of minimizing the adverse effects of a therapeutic antibody in a subject comprising administering an effective amount of an anti-idiotypic antibody of the invention to the subject, wherein the anti-idiotypic antibody specifically binds the therapeutic antibody. In one embodiment, the subject is human. In another embodiment, the therapeutic antibody is abciximab, adalimumab, alemtuzumab, basiliximab, bevacizumab, cetuximab, certolizumab, daclizumab, eculizumab, efalizumab, gemtuzumab, ibritumomab, infliximab, natalizumab, omalizumab, palivizumab, panitumumab, ranibizumab, rituximab, tositumomab, or trastuzumab. In a further embodiment, the therapeutic antibody is rituximab.

In another embodiment of the invention, the adverse effect is depletion of B cells in the subject. In a further embodiment, the first antibody is natalizumab.

In another embodiment of the invention, the adverse effect is progressive multifocal leukoencephalopathy.

In one embodiment, the invention provides a method of neutralizing the immunogenicity of a therapeutic antibody in a subject comprising administering an effective amount of an anti-idiotypic antibody of the present invention that specifically binds the therapeutic antibody.

In one embodiment, the invention provides a method for treating immune thrombocytopenic purpura (ITP) in a subject comprising administering an effective amount of an anti-idiotypic antibody of the present invention that specifically binds one or more anti-platelet auto-antibodies.

In one embodiment, the invention provides a method for treating myasthenia gravis in a subject comprising administering an effective amount of an anti-idiotypic antibody of the present invention that specifically binds one or more anti-acetylcholine receptor auto-antibodies.

In one embodiment, the invention provides a method for treating an autoimmune disease in a subject comprising administering an effective amount of an anti-idiotypic antibody of the present invention that specifically binds one or more auto-antibodies produced by the subject. In one embodiment, the autoimmune disease is Graves disease, experimental autoimmune encephalomyelitis, Addison's Disease, Amyotrophic Lateral Sclerosis, Antiphospholipid Syndrome, Behcet's Disease, Berger's Disease, Crohn's Disease, Cushing's Syndrome, Goodpasture's Disease, Guillian-Barre Syndrome, Hashimoto's Thyroiditis, Kawasaki's Disease, Reiter's Syndrome, Sjogren's Syndrome, Wegener's Granulomatosis, or Wilson's Syndrome.

BRIEF DESCRIPTIONS OF THE DRAWINGS/FIGURES

FIG. 1. Anti-Idiotype Generation Flowchart. NOD mice are immunized simultaneously with antigen (IgG2a isotype antibody) and anti-mCD20 18B12 IgG2a in physiological buffer (i.p. or i.v. administration). Anti-idiotypic antibody titers in the sera are assessed on day 10. A boost of antigen only (IgG2a) is given on day 21, and a traditional hybridoma fusion is performed on day 24.

Figure 2:
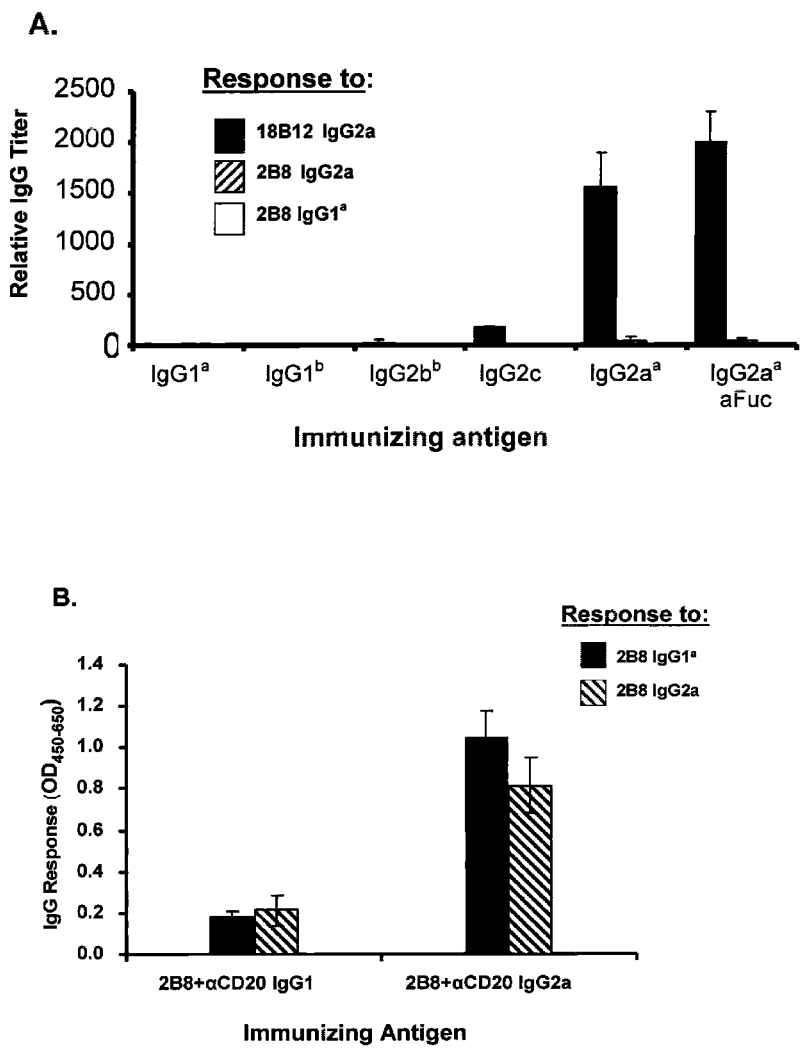

FIG. 2. Dosing of Anti-mCD20 18B12 IgG2a in NOD Mice Generates an Anti-Idiotypic Antibody Response to Anti-mCD20 and a Co-administered Mouse IgG2a. (A) NOD mice (5 per group) were dosed with anti-mCD20 18B12 IgG1a, IgG1b, IgG2b, IgG2a, or afucosyl (aFuc) IgG2a (100 μg in PBS, i.p.). Sera were collected on day 1110 and assessed by ELISA for the presence of anti-idiotypic antibodies to 18B12 IgG2a at various dilution of sera. The 2B8 IgG2a and IgG1a antibodies recognize human CD20 (but not mouse CD20) and were used as controls to detect IgG responses to the γ2a and γ1 isotypes. Bars represent the mean IgG titer as defined in Example 1±SEM for each group. Only animals injected with 18B12 IgG2a generated a strong anti-idiotypic response. A weak anti-idiotypic response to anti-mCD20 18B12 was generated in mice injected with 18B12 IgG2c. (B) NOD mice (4 per group) were dosed with 2B8 IgG2a and either anti-mCD20 18B12 IgG2a or anti-mCD20 18B12 IgG1b (100 μg in PBS i.p. per mouse for each antibody). On day 11 sera were collected and assessed by ELISA for the presence of anti-idiotypic antibodies (1/100 or 1/200 dilution of sera). Bars represent the mean response±SEM for each group. Horizontal dotted line indicates the background signal in the assay in the absence of test sera. Anti-idiotypic antibodies to 2B8 bound similarly to both the IgG1a and IgG2a isotypes of the 2B8 antibody.

Figure 3:
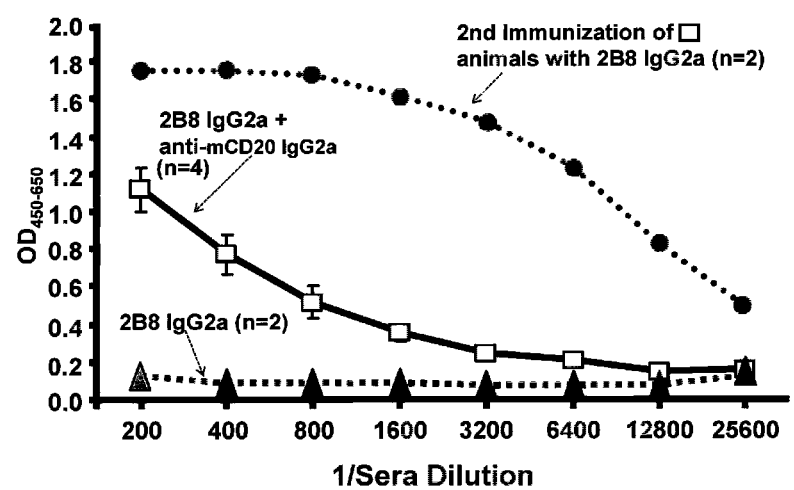

FIG. 3. Anti-Idiotype Response to 2B8 IgG2a is Amplified by Boosting in the Absence of Anti-mCD20. NOD mice were immunized with 2B8 IgG2a alone (triangles) or in conjunction with anti-mCD20 18B12 IgG2a (squares). The anti-mCD20 IgG2a treated animals were boosted 3 weeks later with only 2B8 IgG2a (filled circles). All antibodies were dosed i.p. (100 μg per mouse in PBS). Sera were collected 10 days after each immunization. Specific titers to the 2B8 idiotype were assessed by ELISA on 2B8 IgG1a coated plates. Data points in the n=4 group represent mean±SEM.

Figure 4:
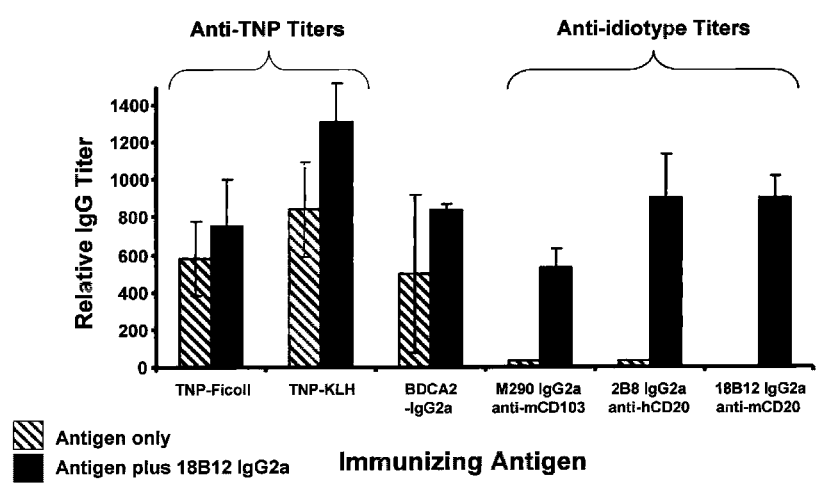

FIG. 4. Enhanced Immunogenicity of Antigens Co-administered with Anti-mCD20 18B12 IgG2a in NOD Mice is Restricted to the Variable Domain (Idiotype) of IgG2a Antibodies. NOD mice (3-4 per group) were immunized with the antigens listed with or without anti-mCD20 18B12 IgG2a (100 μg each per mouse in PBS, i.p.). Mice were bled on day 10 and sera were tested by ELISA for IgG antibodies binding to TNP-Ova (TNP-Ficoll or TNP-KLH immunized animals) or to antigens containing an Fc different from the immunogen (BDCA-2, M290, 2B8, or 18B12 immunized animals). Each bar represents the mean serum titer±SEM.

Figure 5:
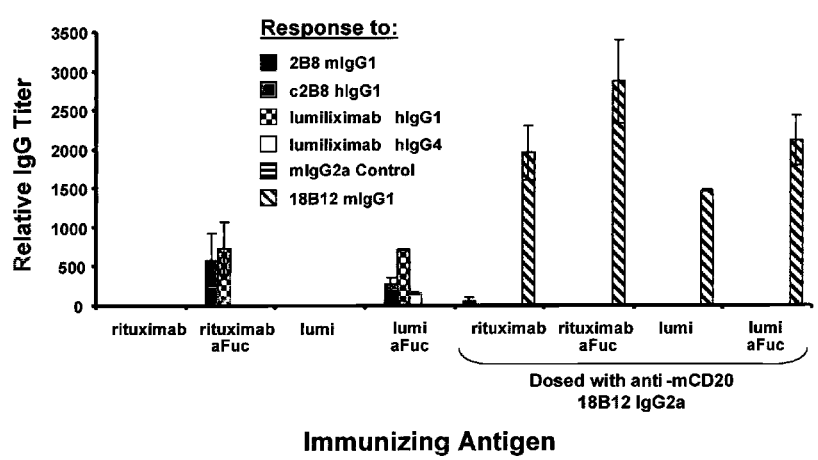

FIG. 5. Co-administration of Anti-Mouse CD20 IgG2a with Human IgG1 Antibodies does not Generate an Anti-Idiotype Response. NOD mice (3 per group) were immunized with or without anti-mCD20 18B12 IgG2a in conjunction with hIgG1 wild type or hIgG1 afucosyl (aFuc) rituximab or lumiliximab (100 μg each antibody per mouse, i.p.). Sera were collected on day 10 and titers were assessed by ELISA to the antigens listed. To absorb non-idiotypic anti-hIgG1 antibodies sera were pre-incubated with CE9.1 (hIgG1 anti-human CD4, 100 µg/ml) for 45 minutes prior to adding to the ELISA plates. Bars indicate the mean titer±SEM. Specific anti-idiotypic antibody titers to rituximab or lumiliximab would have been evident as a response to 2B8 mIgG1 (black bars) or lumiliximab hIgG4 (open bars), respectively. Low titers to c2B8 hIgG1 or lumiliximab hIgG1 in animals not co-administered anti-mCD20 18B12 IgG2a reflect an incomplete absorption by CE9.1 of the dominant immune response to human IgG1. A lack of similar titers in animals dosed with anti-mCD20 18B12 reflects the suppression of the primary immune response to hIgG1 by anti-mCD20-mediated B cell depletion.

Figure 6:
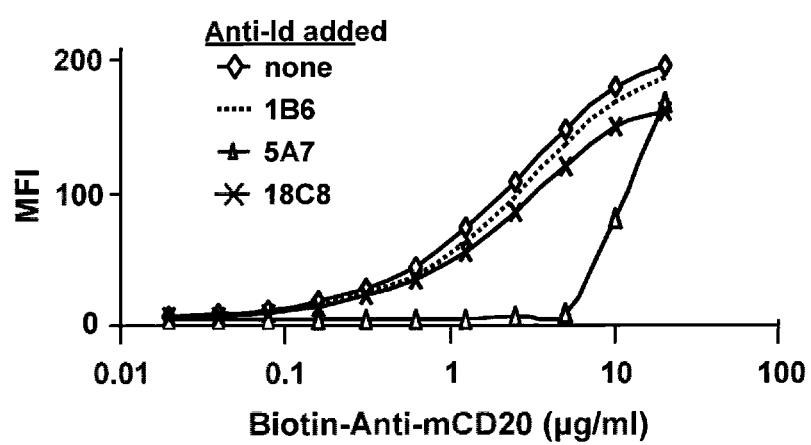

FIG. 6. Anti-Idiotypic Antibodies can be Blocking or Non-Blocking. Dilutions of biotinylated anti-mCD20 18B12 IgG1b were pre-incubated with each of the listed anti-idiotype antibodies (5 µg/ml, 45 minutes). The mixtures were then incubated with mCD20 transfected cells (300.18). Cell bound biotin-anti-mCD20 18B12 was detected using streptavidin-APC and quantified by flow cytometry on a FACSCalibur. MFI, mean fluorescence intensity of CD20+ stained cells. Of the three anti-idiotype antibodies to 18B12 shown here only the 5A7 antibody blocked binding of biotin-18B 12 to mCD20.

Figure 7:
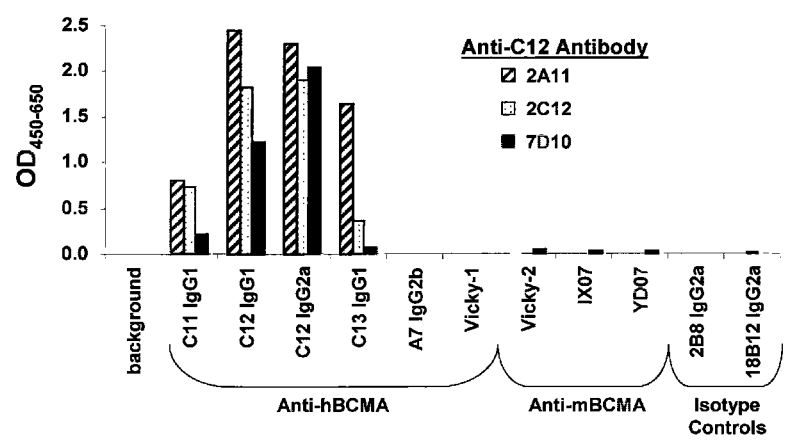

FIG. 7. Anti-idiotype Antibodies can bind Shared Epitopes on Highly Related Monoclonal Antibodies. The three anti-idiotype antibodies to C12 anti-human BCMA, 2A 1, 2C12, and 7D10, were tested by ELISA for binding specificity. Wells of a 96-well plate were coated with either anti-human BCMA (C11 mIgG1, C12 mIgG1, C12 mIgG2a, C13 mIgG1, A2 mIgG2b, or Vicky-1 rat IgG1), anti-mouse BCMA (Vicky-2 rat IgG2a, IX07 rat IgG1, or YD07 rat IgG2a), or isotype control antibodies (2B8 mIgG2a or 18B12 mIgG2a). Purified anti-idiotype antibodies to C12 were tested for binding to coated wells (1 µg/ml each antibody), and detected with biotin-mouse anti-mouse IgG1b (clone B68-2) and streptavidin-horse radish peroxidase. Bars indicate the mean response to each antigen. Each anti-idiotype antibody to C12 showed detectable binding to closely related antibodies C11, C12, and C13 but not to other antibodies tested.

Figure 8:
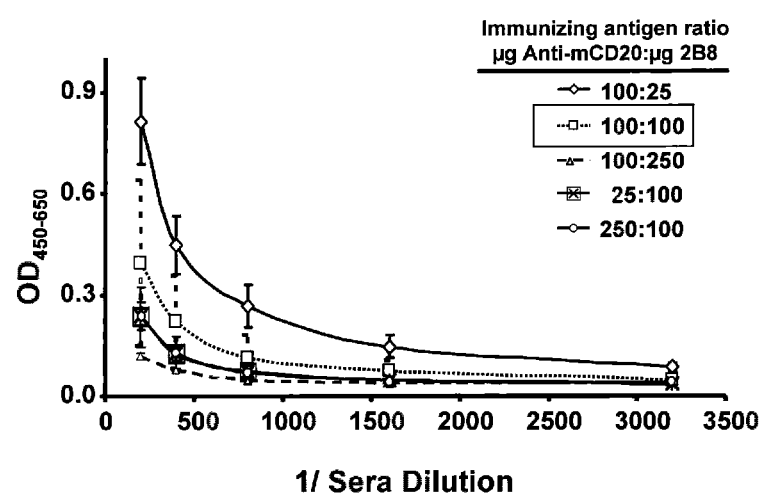

FIG. 8. Determination of the Optimal Ratio of Anti-mCD20 to Antigen. NOD mice (5 per group) were immunized with anti-mCD20 18B12 IgG2a and 2B8 IgG2a in the amounts listed (i.p. in PBS). Mice were bled on day 10 and sera were assessed by ELISA for binding to 2B8 IgG1a. Each point is the mean response of 5 mice+SEM. The boxed antigen ratio (100 µg anti-mCD20:100 µg 2B8) was used for all prior immunizations.

Figure 9:
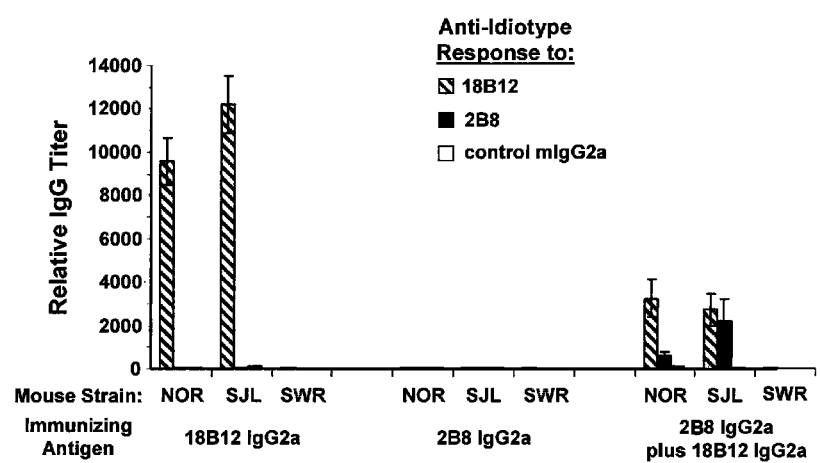

FIG. 9. Anti-Idiotypic Antibody Responses are Generated in NOR and SJL Mice Dosed with 18B12 IgG2a. Mice of the indicated strains were immunized with anti-mCD20 18B12 IgG2a (100 µg, i.p. in PBS), 2B8 IgG2a (100 µg, i.p. in PBS), or both anti-mCD20 18B12 IgG2a and 2B8 IgG2a (100 µg each, i.p. in PBS), bled on day 10, and sera assessed by ELISA for binding to 18B12 IgG1a, 2B8 IgG1a, or control mIgG2a. Each bar is the mean serum IgG titer±SEM of 5 mice/group.

Figure 10:
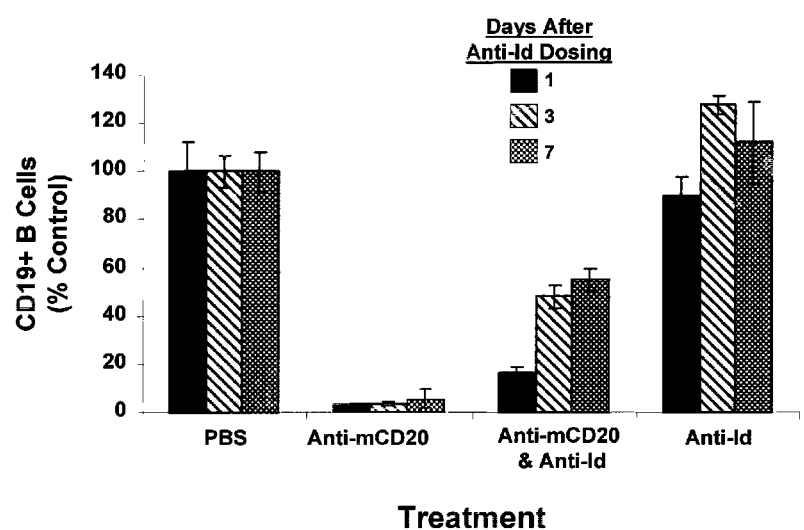

FIG. 10. Administration of Blocking Anti-Idiotype 5A7 to Anti-mCD20 Treated Mice Neutralizes Anti-mCD20 and Initiates B Cell Repopulation. BALB/c mice (4 per group) were dosed with anti-mCD20 18B12 IgG2a (10 mg/kg i.v.) or PBS. Seven days later anti-idiotype antibody 5A7 (250 µg per mouse, i.p.) or PBS was administered. Mice were sacrificed 1, 3, and 7 days after anti-idiotype administration, and peripheral blood mononuclear cells (PBMCs) were analyzed by flow cytometry for CD19+ B cells and CD3+ T cells. Each bar represents the percent CD19+ B cells of the total (CD19+ plus CD3+) lymphocytes (mean±SEM). Percentages were normalized relative to the PBS control group (100%).

Figure 11:
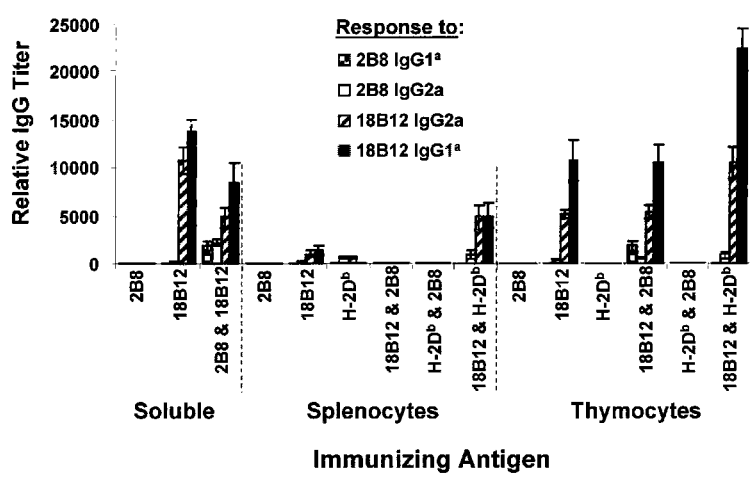
Figure 11:
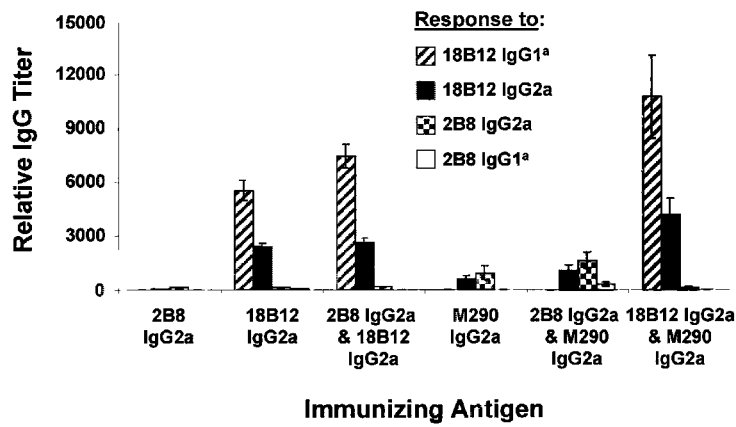

FIG. 11. Anti-mCD20 18B12 Induces an Anti-Idiotype Antibody Response Only when Pre-coated on B Cells or by Soluble Dosage. A. Splenocytes (5×10$^7$; T and B cells) and thymocytes (5×10$^7$; T cells) were coated ex vivo with 18B12 IgG2a or anti-H-2 Db IgG2a (clone 27-11-13S), washed, and injected into NOD mice i.p. with or without soluble 2B8 IgG2a (50 µg). Sera were collected 10 days later and the IgG responses to 2B8 or 18B12 were assessed by ELISA (1/100 dilution of sera). Bars represent the mean serum IgG titer+SEM for 5 mice/group. B. NOD mice (5 per group) were dosed i.p. with untreated or anti-human CD20 2B8 IgG2a treated SKW6.4 cells (human CD20+Burkitt's lymphoma, 1×10$^7$ cells/mouse) with or without 100 µg soluble anti-mCD20 18B12 IgG2a or anti-mCD103 M290 IgG2a. Sera were collected on day 10 and assessed by ELISA for the presence of anti-2B8 or anti-18B12 anti-idiotypic or anti-IgG2a isotype IgG responses. Bars represent the mean serum IgG titers+SEM. Small IgG responses in mice immunized with SKW6.4 cells plus M290 IgG2a or 2B8 IgG2a and M290 IgG2a represent responses to the IgG2a Fc and were not anti-idiotypic IgG responses. The 2B8 IgG2a antibody was unable to elicit an anti-idiotypic antibody response when bound to human B lymphoma cells.

DETAILED DESCRIPTION OF THE INVENTION

The invention provides methods for generating anti-idiotypic antibodies and compositions containing the antibodies. The invention enables the generation of anti-idiotypic monoclonal antibodies having high yields. Details of methods and compositions are provided herein.

By an "anti-idiotypic antibody" is meant an antibody that specifically binds to the antigen-binding site of another antibody and, therefore, is specifically bound by the other antibody. The anti-idiotype antibody can mimic the epitope normally recognized by another antibody. An idiotype is the genetically determined variation of structures in the variable regions of immunoglobulins. The precise genetic basis of idiotype variability has only been partially explained. However, idiotype variation involves the amino acid sequence and protein structure (so-called determinants) especially in the area of the antigen-binding site, also referred to as the idiotope. The term "idiotype" designates the complete set of determinants of a variable region of an antibody molecule.

As used herein, the terms "antibody" and "immunoglobulin" are used interchangeably in the broadest sense and include monoclonal antibodies (e.g., full length or intact monoclonal antibodies), polyclonal antibodies, multivalent antibodies, multispecific antibodies (e.g., bispecific antibodies so long as they exhibit the desired biological activity) and antibody fragments as described herein. The term "bispecific antibody" is intended to include any antibody that has two different binding specificities, i.e. the antibody binds two different epitopes, which can be located on the same target antigen or, more commonly, on different target antigens.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide linkages. Each heavy chain has at one end a variable domain (VH) followed by a number of constant domains. Each light chain has a variable domain at one end (VL) and a constant domain at its other end. In a folded antibody, the constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., J. Mol. Biol. 186, 651-66, 1985); Novotny and Haber, Proc. Natl. Acad. Sci. USA 82, 4592-4596 (1985)). Five human immunoglobulin classes are defined on the basis of their heavy chain constant domain composition, and are named IgG, IgM, IgA, IgE, and IgD. In humans, the IgG-class and IgA-class antibodies are further divided into subclasses, namely, IgG1, IgG2, IgG3, and IgG4, and IgA1 and IgA2. The heavy chains in IgG, IgA, and IgD antibodies have three constant region domains, that are designated CH1, CH2, and CH3, and the heavy chains in IgM and IgE antibodies have four constant region domains, CH1, CH2, CH3, and CH4. Thus, heavy chains have one variable region and three or four constant regions. Immunoglobulin structure and function are reviewed, for example, in Harlow et al., Eds., Antibodies: A Laboratory Manual, Chapter 14, Cold Spring Harbor Laboratory, Cold Spring Harbor (1988).

"Antibody fragments" comprise only a portion of an intact antibody, wherein the portion preferably retains at least one, preferably most or all, of the functions normally associated with that portion when present in an intact antibody.

The term "monoclonal antibody" as used herein refers to an antibody obtained from a population of substantially homogeneous antibodies, i.e., the individual antibodies comprising the population are of identical amino acid sequence except for possible naturally occurring mutations that may be present in minor amounts. Monoclonal antibodies are highly specific and bind a single antigen. Furthermore, in contrast to polyclonal antibody preparations that typically include different antibodies directed against different determinants (epitopes), each monoclonal antibody is directed against a single determinant on the antigen. That an antibody "selectively binds" or "specifically binds" means that the antibody reacts or associates more frequently, more rapidly, with greater duration, with greater affinity, or with some combination of the above to an epitope than with alternative substances, including unrelated proteins. "Selectively binds" or "specifically binds" means, for instance, that an antibody binds to a protein with a KD of at least about 0.1 mM, but more usually at least about 1 µM. "Selectively binds" or "specifically binds" means at times that an antibody binds to a protein at times with a KD of at least about 0.1 µM or better, and at other times at least about 0.01 µM or better. For example, an anti-idiotype antibody desirably has an affinity for its antigen that is least 2-fold, 5-fold, 10-fold, 30-fold, or 100-fold greater than for an equal amount of any other antigen, including related antigens. Binding of a polypeptide to another polypeptide may be determined as described herein, and by any number of standard methods in the art, e.g., Western analysis, ELISA, fluorescence polarization, surface plasmon resonance, or co-immunoprecipitation.

The terms "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable vehicle" refers to a diluent, adjuvant, excipient, or carrier with which at least one antibody of the present disclosure is administered.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The antibodies of the present invention can be used to treat a variety of disorders. A "disorder" is any condition that would benefit from treatment with an antibody or method of the invention. This includes chronic and acute disorders or diseases including those pathological conditions that predispose the mammal to the disorder in question. Non-limiting examples of disorders to be treated herein include autoimmune disease, inflammation, cell proliferative disorders; B cell lymphomas, non-leukemias and lymphoid malignancies; neuronal, glial, astrocytal, hypothalamic and other glandular, macrophagal, epithelial, stromal and blastocoelic disorders; and inflammatory, immunologic, or infectious diseases. The terms "cell proliferative disorder" and "proliferative disorder" refer to disorders that are associated with some degree of abnormal cell proliferation. In one embodiment, the cell proliferative disorder is cancer.

As used herein, the term "autoimmune disease" refers generally to diseases which are characterized as having a component of self-recognition. Examples of autoimmune diseases include, but are not limited to, Autoimmune hepatitis, Multiple Sclerosis, Systemic Lupus Erythematosus, Idiopathic Thrombocytopenic Purpura, Myasthenia Gravis, Type I diabetes, Rheumatoid Arthritis, Psoriasis, Hashimoto's Thyroiditis, Grave's disease, Ankylosing Spondylitis Sjogrens Disease, CREST syndrome, Scleroderma, IgA Neprhopathy, Bullous Pemphigoid, Pemphigous Vulgaris, ANCA-Associated Vasculitis, Antiphospholipid Syndrome and many more. Most autoimmune diseases are also chronic inflammatory diseases. This is defined as a disease process associated with long-term (>6 months) activation of inflammatory cells (leukocytes). The chronic inflammation leads to damage of patient organs or tissues. Many diseases are chronic inflammatory disorders, but are not known to have an autoimmune basis. For example, Atherosclerosis, Congestive Heart Failure, Crohn's disease, Ulcerative Colitis, Polyarteritis nodosa, Whipple's Disease, Primary Sclerosing Cholangitis and many more.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or disorder.

An "effective amount" refers to an amount effective, at dosages and for periods of time necessary, to achieve the desired therapeutic or prophylactic result. A "therapeutically effective amount" of an antibody of the invention can vary according to factors such as the disease state, age, sex, and weight of the individual, and the ability of the antibody to elicit a desired response in the individual. A therapeutically effective amount is also one in which any toxic or detrimental effects of the antibody are outweighed by the therapeutically beneficial effects.

In one embodiment, the invention provides an in vivo method for the rapid generation of diverse panels of mouse anti-idiotypic monoclonal antibodies. In certain embodiments, the methods are performed in mice. In further embodiments, the mice are susceptible to autoimmune disease (e.g. utilizing the Non-Obese Diabetic (NOD) strain of mice). NOD mice, like C57BL/6, 129, and SJL strains, express the Igh-1b allele of γ2a, also known as γ2c, which in this unusual case of the Igh-1 locus, is encoded by a gene distinct from the Igh-1a allele that is differentially expressed with the Igh-1a gene (Martin et al., 1997). Unlike other H chain alleles, which differ from each other by only one or several amino acids, the Igh-1a and Igh-1b gene products, γ2a and γ2c, respectively, are only 85% identical in their H chain C regions (Morgado et al., 1989). Strains of mice useful in the methods of the invention can be obtained from commercial sources (e.g. The Jackson Laboratory, Bar Harbor, Me.).

In one embodiment, the invention provides a method for generating anti-idiotypic antibody that requires administration of an antibody that binds a B cell surface antigen. B cell surface antigens include, but are not limited to CD19, CD20, CD21, and CD23. In one embodiment, the targeted antibody binds a B cell surface antigen and contains a γ2a H chain C region. In one embodiment, the invention provides a method for generating anti-idiotypic antibodies in mice that requires that the targeted antibody (antigen) contains a γ2a H chain C region and be administered concurrently with 18B12 IgG2a, a mouse anti-mCD20 antibody also containing a γ2a H chain C region. Mice administered a single dose of 18B12 IgG2a in physiological buffer produced a strong anti-idiotypic response to the anti-mCD20 18B 12 antibody. Co-administration of 18B12 IgG2a with an IgG2a antibody different from anti-mCD20 18B12 resulted in an anti-idiotypic antibody response to both proteins. In some embodiments, anti-idiotype responses to both antibodies were rapidly generated, appearing within 10 to 11 days of primary immunization. The titer to the second IgG2a antibody could be increased by subsequent immunizations with the IgG2a antigen in the absence of anti-mCD20 18B12 antibody. Optimal amounts of anti-mCD20 18B12 IgG2a and immunizing IgG2a antigen were established to give the best anti-idiotypic antibody titers. Several autoimmune-prone Igh-1b mouse strains closely related to NOD were also found to generate similar anti-idiotypic antibody responses to 18B12 IgG2a and an immunizing IgG2a antigen. Using a standard hybridoma fusion protocol, diverse panels of monoclonal anti-idiotypic antibodies to a target antibody were generated.

In another aspect of the invention, the antibodies can be chemically or biosynthetically linked to detectable signal-producing agents. Detectable signal-producing agents are useful in vivo and in vitro for diagnostic purposes, and can also be used to detect the amount of a first therapeutic antibody remaining in a sample. The signal producing agent produces a measurable signal which is detectible by external means, usually the measurement of electromagnetic radiation. For the most part, the signal producing agent is an enzyme or chromophore, or emits light by fluorescence, phosphorescence or chemiluminescence. Chromophores include dyes that absorb light in the ultraviolet or visible region, and can be substrates or degradation products of enzyme catalyzed reactions.

Alleviation of Side Effects

Therapeutic antibodies can have a wide array of side or adverse effects. Possible adverse effects include, but are not limited to, hypertension, leukoencephalopathy, decrease in immune surveillance and depletion of B cells.

The invention provides compositions and methods utilizing an anti-idiotypic antibody that reduces or eliminates a side effect associated with therapeutic antibody treatment. Without being limited to any theory, one possible mechanism by which the adverse effects are eliminated is that the anti-idiotypic antibody binds the therapeutic antibody, inhibits the therapeutic antibody from binding to its antigen or by complexing with the antibody and hastening its clearance from circulation. In this way, the modulatory effect of the anti-idiotypic antibody can be dose-dependent.

In certain embodiments, since the anti-idiotypic antibodies specifically bind to the therapeutic antibody, the anti-idiotypic antibody can be used to shorten the half-life of a therapeutic drug or drug conjugate. In certain embodiments, a subject is administered a bolus dose of a therapeutic agent. Following a prescribed period of time, the anti-idiotypic antibody is then administered. Administration of the anti-idiotypic antibody reduces the half-life of the therapeutic agent by leading to faster clearance. In certain embodiments, faster clearance of the therapeutic agent leads to repopulation of certain cell types or return of certain biological functions, such as humoral response to neo-antigens. In one embodiment, clearance of the therapeutic agent leads to repopulation of B cells.

The adverse effect may be acute or chronic. The effect may be biochemical, cellular, at the tissue level, at the organ level, at the multi-organ level, or at the level of the entire organism. The effect may manifest in one or more objective or subjective manners, any of which may be used to measure the effect. If an effect is measured objectively or subjectively, any suitable method for evaluation of objective or subjective effect may be used. Examples include visual and numeric scales and the like for evaluation by an individual.

Antibodies of the present invention can be administered in conjunction with other compounds useful in the treatment of disorders such as autoimmune diseases. The other compounds, for example a therapeutic antibody, can be administered concurrently. As used herein, the word "concurrently" means sufficiently close in time to produce a combined effect (that is, concurrently may be simultaneously, or it may be two or more events occurring within a short time period before or after each other).

As used herein, the administration of two or more antibodies "concurrently" or "in combination" means that the two antibodies are administered closely enough in time that the presence of one alters the biological effects of the other. The two antibodies may be administered simultaneously or sequentially. Simultaneous administration may be carried out by mixing the antibodies prior to administration, or by administering the compounds at the same point in time but at different anatomic sites or using different routes of administration.

The anti-idiotypic antibodies can be administered to neutralize the side-effects of a primary therapeutic treatment to a patient suffering from a disorder. In certain embodiments, the anti-idiotypic antibodies are administered to a patient who is receiving a therapeutic antibody or antibody fragment as a therapy. The anti-idiotypic antibodies are administered in an amount sufficient to neutralize the side-effects of the primary therapy. An amount adequate to accomplish this is defined as a therapeutically effective dose. Amounts effective for this use will depend upon the severity of the disease and the general state of the patient's own immune system. Dosing schedules will also vary with the disease state and status of the patient, and will typically range from a single bolus dosage or continuous infusion to multiple administrations per day (e.g., every 4-6 hours), or as indicated by the treating physician and the patient's condition. Antibodies of the invention can be administered in a single dosage as high as 40 mg/kg body-weight or higher. More preferably, the antibodies are administered in dosages that range from 0.2 mg/kg to 20 mg/kg body-weight. It should be noted, however, that the present invention is not limited to any particular dose.

Formulations of the anti-idiotypic antibodies are prepared for storage and use by combining a purified antibody of the present invention with a pharmaceutically acceptable vehicle (e.g. carrier, excipient) (Remington, The Science and Practice of Pharmacy 20th Edition Mack Publishing, 2000). Suitable pharmaceutically acceptable vehicles include, but are not limited to, nontoxic buffers such as phosphate, citrate, and other organic acids; salts such as sodium chloride; antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosacchandes, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and non-ionic surfactants such as TWEEN or polyethylene glycol (PEG).

The pharmaceutical composition of the present invention can be formulated in unit dosage form and administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); or parenteral including intravenous, intraarterial, subcutaneous, intraperitoneal or intramuscular injection or infusion; or intracranial (e.g., intrathecal or intraventricular) administration.

For the treatment of the disease, the appropriate dosage of the anti-idiotypic antibody of the present invention depends on the adverse effect to be neutralized, the severity and course of the effect, the responsiveness of the disease, whether the anti-idiotypic antibody is administered for therapeutic or preventative purposes, previous therapy, patient's clinical history, and so on all at the discretion of the treating physician. The anti-idiotypic antibodies can be administered one time or over a series of treatments lasting from several days to several months, or until a cure is effected or a diminution of the disease state is achieved. Optimal dosing schedules can be calculated from measurements of drug accumulation in the body of the patient and will vary depending on the relative potency of an individual antibody. The administering physician can easily determine optimum dosages, dosing methodologies and repetition rates. In general, dosage is from 0.01 µg to 100 mg per kg of body weight, and can be given once or more daily, weekly, monthly or yearly. The treating physician can estimate repetition rates for dosing based on measured residence times and concentrations of the drug in bodily fluids or tissues.

In Vitro Diagnostic Assays

The anti-idiotype antibodies of the present invention may be used in a variety of diagnostic assays to determine whether a subject expresses an antibody or an antigen that specifically binds the anti-idiotype antibody. As an anti-idiotype antibody can mimic an antigen expressed by a neoplastic cell and not by a non-neoplastic cell, the anti-idiotype antibody may, for example, be used as a control antigen for enzyme-linked immunosorbent assay (ELISA), Western blotting, or in situ detection of tumor cells in a tissue sample. Moreover, one skilled in the art may use an anti-idiotype antibody to determine whether a patient expresses an antibody that specifically binds to the anti-idiotype antibody. In another assay, the anti-idiotype antibody can be used to measure the amount of the first therapeutic antibody that remains in the serum of the subject being treated. Other assays in which an anti-idiotype antibody of the invention may be used include, immunohistochemical staining and fluorescence activated cell sorting (FACS).

An ELISA assay typically involves the use of a polypeptide, such as an anti-idiotype antibody, immobilized on a solid support to bind to a biological sample, e.g., one containing antibodies from a cancer patient. If antibodies from the biological sample bind the anti-idiotype antibody, the bound antibodies may then be detected using a detection reagent that contains a reporter group and that specifically binds to the antibody/anti-idiotype antibody complex. Such detection reagents include, for example, any binding agent that specifically binds to an antibody, such as an anti-immunoglobulin, protein G, protein A, or a lectin. Alternatively, a competitive assay may be utilized, in which an antibody that specifically binds the anti-idiotype antibody is labeled with a reporter group and allowed to bind to the immobilized anti-idiotype antibody after incubation of the anti-idiotype antibody with the biological sample. The extent to which components of the sample inhibit the binding of the labeled antibody to the anti-idiotype antibody is indicative of the reactivity of a component of the sample with the immobilized anti-idiotype antibody.

The method employed for detecting the reporter group depends upon the nature of the reporter group. For radioactive groups, scintillation counting, PET scanning, or autoradiographic methods may be used. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a defined period of time), followed by spectroscopic or other analysis of the reaction products.

In one aspect, the invention provides for an in vitro diagnostic assay which is useful for monitoring the levels of a first antibody in a subject or for identifying whether a subject is at risk for developing an autoimmune disease. The diagnostic assay includes the steps of (1) obtaining an amount of serum from the subject to be tested; (2) determining the level of the levels of a first antibody, or another autoimmune disease marker in the subject's serum sample using any known method; (3) comparing the antibody or disease marker measured in the subject's serum with the level of each factor determined to exist in a serum sample taken from an age-matched and gender-matched normal healthy subject; (4) identifying whether the levels measured from the subject to be tested are higher or lower than those of the healthy subject thereby monitoring the status of the autoimmune disease in the subject or assessing the risk of the subject for developing an autoimmune disease.

The invention is also directed to an in vitro assay for determining a subject's risk for developing an autoimmune disease which comprises (1) obtaining a serum sample from the subject; (2) quantifying the level of the levels of a first antibody, or another autoimmune disease marker in the subject's serum sample using any known method; (3) comparing the antibody or disease marker measured in the subject's serum with the level of each factor determined to exist in a serum sample taken from an age-matched and gender-matched normal healthy subject; (4) identifying whether the levels measured from the subject to be tested are higher or lower than those of the healthy subject. A high risk of developing an autoimmune disease is indicated by quantities in step (2) supra which are within a 30% range of the quantities measured for the subject with an autoimmune disease. This risk increases when quantities are 20% of normal. In another aspect of the invention, the subjects can be age-matched.

The invention is also directed to a kit for determining a subject's risk for developing an autoimmune disease or for monitoring the status of an autoimmune disease in a subject which comprises a composition which specifically binds to first antibody or autoimmune disease marker in a biological sample from a subject, and wherein the composition is detectable. The detectable marker includes but is not limited to a fluorescent marker, a radioactive marker, an enzymatic marker, a colorimetric marker, a chemiluminescent marker or any combination thereof.

In one embodiment of the invention, the biological sample is a blood sample or a serum sample. In another embodiment of the invention, the kit further comprises components for correlating the quantity of composition bound to the biological sample to a relative risk of developing an autoimmune disease or a relative status of an autoimmune disease. In another embodiment of the invention, the composition is labeled with a detectable marker. The detectable marker can be, but is not limited to, a fluorescent marker, a radioactive marker, an enzymatic marker, a colorimetric marker, a chemiluminescent marker and any combination thereof. The kit can also include components for standardization or normalization among samples to insure that the diagnostic assays are comparing relatively equivalent numbers of cells or volumes of serum.

In addition, the invention also provides for an in vitro assay for determining a subject's risk for developing an autoimmune disease which comprises: (a) obtaining a serum sample from the subject; (b) admixing the serum with monocytes in vitro under conditions suitable for monocyte differentiation; (c) measuring the ability of the subject's serum to induce differentiation of monocytes into dendritic cells which are capable of presenting antigen; and (d) comparing the ability measured in step (c) with (i) the ability of serum taken from a healthy subject and with (ii) the ability of serum taken from a subject suffering from an autoimmune disease, thereby determining the subject's risk for developing an autoimmune disease.

In another aspect, the present invention is an in vitro diagnostic assay by which a patient's risk of developing autoimmune disease can be determined and monitored. This diagnostic assay measures the ability of patient's serum to induce monocyte differentiation into dendritic cells in vitro in order to assess the risk that patient has for developing an autoimmune disease. In this regard, if the patient's serum induces differentiation of monocytes to dendritic cells more effectively than the known normal standard (which can be determined by using serum from several age-matched, gender-matched, healthy individuals), the assay is predictive of a disease flare in patients with autoimmune disease and/or indicative of the necessity for detailed diagnostic evaluation whether the patient is at risk of developing an autoimmune disease. In addition, the diagnostic assay is useful to monitor a patient's disease condition, if the patient has already been diagnosed with an autoimmune disease, the patient can utilize the diagnostic assay of the present invention to monitor the progress or improvement of the autoimmune disease and adjust his/her treatment regimen accordingly.

The present invention provides kits comprising the anti-idiotypic antibodies described herein and kits that can be used to perform the methods described herein. In certain embodiments, a kit comprises at least one purified anti-idiotype antibody against a therapeutic antibody in one or more containers. One skilled in the art will readily recognize that the disclosed antibodies of the present invention can be readily incorporated into one of the established kit formats that are well known in the art.

Embodiments of the present disclosure can be further defined by reference to the following examples that describe in detail the preparation and methods for using the anti-idiotype antibodies of the present disclosure. It will be apparent to those skilled in the art that many modifications, both to materials and methods, can be practiced without departing from the scope of the present disclosure. Wherever possible, the same reference numbers will be used throughout the drawings to refer to the same or like parts. As used herein and in the appended claims, the singular forms "a," "or," and "the" include plural referents unless the context clearly dictates otherwise. Thus, for example, reference to "an antibody" includes a plurality of such antibodies or one or more antibodies and equivalents thereof known to those skilled in the art. Furthermore, all numbers expressing quantities of ingredients, reaction conditions, purity, polypeptide and polynucleotide lengths, and so forth, used in the specification, are modified by the term "about," unless otherwise indicated. Accordingly, the numerical parameters set forth in the specification and claims are approximations that can vary depending upon the desired properties of the present invention.

All of the various embodiments or options described herein can be combined in any and all variations.

EXAMPLES

Example 1

Experimental Procedures

Generation of Mouse Anti-Mouse CD20 18B12. Generation of the mouse anti-mCD20 hybridoma 18B12 and its isotype variants was as described in Patent Application US 2007/0136826 A1, incorporated herein by reference.

Mice. NOD (male and female), female SJL, male SWR, male NOR, male C.B-17, male C57BL/6, and BALB/c mice (male and female) were purchased from the Jackson Laboratories (Bar Harbor, Me.) and housed in the animal facility at Biogen Idec. NOD, NOR, SJL, and C.B-17 mice express the Igh-1b allele of IgG2a (IgG2c); BALB/c mice express the Igh-1a allele (IgG2a); and SWR mice express the Igh-Ic gene. NOR mice are a recombinant congenic strain in which limited regions (~15%) of the NOD genome have been replaced by genome from the C57BL/KsJ strain in order to map diabetes-related genes (Serreze et al., 1994). Mice were between 8-12 weeks old at the start of all studies. NOD mice were used for all anti-idiotypic antibody generation studies except as noted. BALB/c mice were used to assess the effectiveness of in vivo neutralization of 18B12 antibody by anti-idiotype monoclonal antibody 5A7. All animal protocols were reviewed and approved by the Biogen Idec Institutional Animal Care and Use Committee (IACUC).

TABLE 1

Antibodies and IgG-Fusion Proteins Used for Immunization and Screening

| Binding Specificity | Name | Isotype | Species (Fc) | Cell Line |
|---|---|---|---|---|
| mouse CD20 | 18B12 | IgG1$^a$ | mouse | CHO |
|  | 18B12 | IgG1$^b$ | mouse | hybridoma |
|  | 18B12 | IgG2a | mouse | CHO |
|  | 18B12 | IgG2b | mouse | hybridoma |
|  | 18B12 | IgG2c | mouse | hybridoma |
| human CD20 | 2B8 | IgG1$^a$ | mouse | CHO |
|  | 2B8 | IgG2a | mouse | CHO |
|  | rituximab | IgG1 | human | CHO |
|  | afuc rituximab | IgG1 afucosyl | human | CHO |
| human BCMA | C12 | IgG1 | mouse | hybridoma |
|  | C12 | IgG2a | mouse | CHO |
| human CD23 | lumiximab | IgG1 | human | CHO |
|  | afuc lumi | IgG1 afucosyl | human | CHO |
|  | γ4 lumiliximab | IgG4 | human | CHO |
| unknown | BDCA2-Ig | IgG2a | mouse | CHO |
|  | BDCA2-Ig | IgG1 | human | CHO |
| mouse CD 103 | M290 | IgG2a | mouse | CHO |
|  | M290 | IgG1 aglycosyl | mouse | CHO |

Immunizations and Hybridoma Production. Antibodies and proteins used as antigens for immunization in combination with anti-mCD20 18B12 IgG2a and for hybridoma screening are listed in Table 1. For the production of anti-idiotypic antibodies to the 18B12 antibody a single administration of anti-mCD20 18B12 IgG2a in phosphate buffered saline (PBS) was given to 10 NOD mice (100 μg intraperitoneally (i.p.)). On day 7 mice were bled and sera assessed by ELISA for anti-idiotypic antibody binding to 18B12 IgG1$^a$. The mouse with the highest titer was selected for hybridoma fusion the next day (day 8; Köhler and Milstein, 1975). For the generation of anti-idiotypic antibodies to the 2B8, C12 and M290 antibodies, five NOD mice were initially immunized with each antigen: 18B12 IgG2a and 2B8 IgG2a (100 μg each i.p. in PBS), 18B12 IgG2a and C12 IgG2a (100 μg 18B12 IgG2a and 25 μg C12 IgG2a, each i.p. in PBS) or 18B12 IgG2a and M290 IgG2a (100 μg each i.p. in PBS). Mice were bled on day 10 and sera assessed by ELISA for antibodies specifically binding the variable domains of the 2B8, C12 or M290 antibodies. Mice were rested and then boosted on day 21 with either 2B8 IgG2a or M290 IgG2a (100 μg i.p. in PBS) or on day 17 with C12 IgG2a (50 μg i.p. in PBS). A hybridoma fusion was performed 3 days later (Köhler and Milstein, 1975). The general scheme for anti-idiotypic antibody generation is shown in FIG. 1.

Each hybridoma fusion utilized a standard protocol (Köhler and Milstein, 1975) with PEG1500 (Sigma Chemical Co., St. Louis, Mo.) and either NS-1 or SP2/0 myeloma fusion partners. The NS-1 fusion partner (non-secreting clone of P3X63Ag8; American Type Culture Collection, Manassas, Va.) was used for the anti-18B12 and anti-C12 fusions. For anti-2B8 the spleen cells were divided into two equal parts and either the SP2/0 (Sp2/0-Ag14; ATCC) or NS-1 myeloma fusion partner was used. The SP2/0 fusion partner was used for the anti-M290 fusion. Hybridomas were plated in Iscove's Modified Dulbecco's Medium (Mediatech, Manassas, Va.) supplemented with 10% fetal bovine serum (FBS), L-glutamine (Gibco-BRL, Bethesda, Md.), non-essential amino acids (Sigma Chemical Co), sodium pyruvate (Sigma Chemical Co.), gentamicin (Gibco-BRL), and Hybridoma Fusion and Cloning Supplement (Roche Diagnostics, Mannheim, Germany). Hybridomas meeting the screening criteria of binding to all immunogen isotypes but not to isotype control antibodies were subcloned by limiting dilution, expanded, and antibody purified from culture supernatants using Protein A chromatography.

Flow Cytometry and ELISA Reagents. Biotin-anti-mouse IgG1b (B68-2), biotin-anti-mouse IgG2ab (5.7), biotin-anti-IgG2aa (8.3), FITC-anti-CD3 (145-2C11), PE-anti-CD19 (1D3), unconjugated anti-CD16/CD32 (2.4G2), Streptavidin-HRP, and Streptavidin-APC were obtained from BD-Pharmingen (San Diego, Calif.). Biotin-anti-IgG2b (LO-MG2b) was purchased from Southern Biotechnologies (Birmingham, Ala.). 7AAD was from Molecular Probes (Eugene, Oreg.). TNP-KLH, TNP-Ficoll, and TNP-Ova were obtained from Biosearch Technologies, Inc. (Novato, Calif.). Antibodies used for coating ELISA plates are listed in Table 1.

Cell Staining and Flow Cytometry Analyses. All staining procedures were done in round bottom 96-well plates (Corning 3799) in FACS buffer (Dulbecco's PBS without calcium and magnesium supplemented with 2% FBS, 0.05% sodium azide, 10% normal goat serum (heat inactivated)), and, when mouse cells were used, 2.4G2 antibody (5-10 μg/ml). Cells (between 0.1×106 and 1×106 per sample) were incubated with primary or secondary antibodies for 45 minutes on ice, washed twice between incubations, and resuspended at 3–5×106 cells/ml in FACS buffer for analyses. Fluorescence was measured on a FACSCalibur or FACSCanto (BD Biosciences, San Jose, Calif.) and analyzed with BD FACSDiva™ or BD CellQuest Pro software (BD Biosciences).

ELISA Assays. Hybridoma supernatants were screened by ELISA for binding to other isotypes of the immunizing antigen that were different from the IgG2a immunogen as well as for binding to a panel of isotype control antibodies. Briefly, microtiter wells (Immulon2 HB 96-well plates; Thermo Labsystems, Franklin, Mass.) were coated with the appropriate antigen or isotype control antibody (2 μg/ml in 0.1 M sodium bicarbonate pH 9.6; 100 μl/well; overnight at 4° C.). Bound hybridoma antibodies were detected with a pool of three biotinylated anti-IgG reagents that recognize the three major IgG isotypes (IgG1b, IgG2b, and IgG2c) expressed by NOD mice. Using this strategy the antibodies used for coating the ELISA plate wells were not detected. Biotinylated reagents were detected with streptavidin-HRP followed by the addition of a TMB substrate (KPL, Gaithersburg, Md.). After a 5 minute development at room temperature the reaction was quenched with an equal volume of 4N sulfuric acid and plates read on a Spectramax plate reader at 450 nm with a 650 nm reference (Molecular Devices, Palo Alto, Calif.). Serum titers were defined as 1/dilution of serum resulting in an $OD_{450-650}$ of 0.5.

Example 2

Anti-mCD20 IgG2a Isotype Generates an Amplifiable Anti-Idiotypic Antibody Response in NOD Mice To test whether the anti-idiotypic antibody response in NOD mice to anti-mCD20 18B12 IgG2a required the IgG2a Fc NOD mice were dosed with either anti-mCD20 18B12 IgG1a, IgG1b, IgG2b, IgG2c, IgG2a, or anti-mCD20 18B12 afucosyl IgG2a and the sera examined for antibody titers to the 18B 12 variable domains. Antibodies were administered in PBS without the adjuvant frequently used during anti-idiotype immunizations. Assessment of sera titers on day 10 post-dosing identified a strong titer of anti-idiotypic IgG antibodies generated to anti-mCD20 18B12 variable domains in mice dosed with 18B12 IgG2a or 18B12 afucosyl IgG2a, but not in those mice dosed with anti-mCD20 18B12 IgG1a, IgG1b, or IgG2b (FIG. 2A). A weak anti-idiotypic IgG response to anti-mCD20 18B12 variable domains was found in mice dosed with anti-mCD20 18B12 IgG2c.

Additionally, we investigated whether the anti-idiotypic antibody response was restricted to 18B12 itself or could be generated by or be extended to a "bystander" mouse IgG2a antibody not binding to mouse CD20. NOD mice were dosed with anti-mCD20 18B12 (IgG2a or IgG1b) in conjunction with another mouse IgG2a (2B8, mouse anti-hCD20). Mice co-administered the 2B8 IgG2a antibody and anti-mCD20 18B12 IgG2a generated an anti-idiotypic response to both 18B12 antibody (not shown) and 2B8 antibody (FIG. 2B). In contrast, mice co-administered the 2B8 IgG2a antibody with the anti-mCD20 18B 12 IgG1b did not make a detectable anti-idiotypic antibody response to either antibody (FIG. 2B).

Since these anti-idiotypic antibody responses in NOD mice represented primary antibody responses that are typically of lower affinity, we wanted to test whether this primary anti-idiotypic response generated amplifiable humoral memory. To avoid anaphylaxis that resulted after more than one injection of NOD mice with the 18B12 IgG2a antibody the secondary anti-idiotypic antibody response to 2B8 was followed. As expected, when the 2B8 IgG2a was co-administered with anti-mCD20 18B12 IgG2a a primary anti-idiotype titer to 2B8 was generated by day 10 (FIG. 3, open squares). No anti-idiotypic antibody response was found in mice dosed with 2B8 IgG2a alone (FIG. 3, triangles) or dosed with 2B8 IgG2a and anti-mCD20 IgG1 (not shown—see FIG. 2). After three weeks (day 31) mice previously dosed with 2B8 IgG2a and anti-mCD20 18B12 IgG2a were boosted with only 2B8 IgG2a. Sera collected 10 days after the second immunization were assayed for IgG anti-idiotypic antibodies to the 2B8 variable domain. A humoral memory response was evident with a ~32 fold increase in anti-idiotype sera titers to 2B8 as compared with the primary response (FIG. 3, compare open squares and filled circles).

Example 3

Enhanced Immunogenicity of Antigens Co-Administered with Anti-mCD20 IgG2a in NOD Mice is Restricted to Variable Domains of Mouse IgG2a Antibodies To test whether the enhanced idiotype immunogenicity found in NOD mice after anti-mCD20 IgG2a treatment could be expanded to antigens that were not intact antibodies, mice were immunized with trinitrophenyl (TNP)-KLH (keyhole limpet hemocyanin) and TNP-Ficoll (T-dependent and T-independent antigens, respectively) with or without anti-mCD20 IgG2a co-administration. Additionally, a fusion protein comprised of the extracellular domain of human BDCA2 linked to the mIgG2a Fc and a rat anti-mouse CD103 antibody engineered as a chimeric mouse IgG2a antibody were selected for co-immunization with anti-mCD20 IgG2a. TNP conjugates and human BDCA2, as expected, were immunogenic in the absence of anti-mCD20 IgG2a treatment (FIG. 4). Co-administration of anti-mCD20 IgG2a did not significantly increase their immunogenicity (FIG. 4) although there was a (non-significant) trend towards higher titers in the anti-mCD20-treated animals. As found previously with co-administered 2B8 IgG2a and 18B12 IgG2a antibodies, an anti-idiotypic response was generated to antibodies with a mouse γ2a Fc region only when they were co-administered with anti-mCD20 18B12 IgG2a (FIG. 4).

Since the anti-idiotypic antibody response was restricted to mouse IgG2a antigens a possible role of mouse Fcγ Receptor (FcγR) engagement in antigen uptake/processing was explored by immunizing NOD mice with an afucosyl human IgG 1 (hIgG1). The binding affinity of afucosyl hIgG1 antibodies to mouse FcγRIV, the FcγR that primarily binds mouse IgG2a and IgG2b (Nimmerjahn and Ravetch, 2006), appears to be similar to the binding affinity of mouse IgG2a to FcγRIV. The possibility that an afucosyl hIgG1 target antigen might behave similarly to mouse IgG2a was tested by dosing NOD mice with hIgG1 or afucosyl hIgG1 variants of c2B8 (rituximab, anti-human CD20) or lumiliximab (anti-human CD23, Primatized® from the 5E4 cynomolgus monoclonal antibody) alone or in conjunction with anti-mCD20 18B12 IgG2a. To minimize the expected high background response to hIgG1 and enable detection of a true anti-idiotype response, sera from immunized NOD mice were diluted (1/100) and absorbed with a different hIgG1 antibody, CE9.1 (anti-human CD4, 100 µg/ml). An anti-idiotype response was specifically detected by testing sera for binding to c2B8 and lumiliximab containing Fc region isotypes different from the immunizing antigen (mouse IgG1 and human IgG4, respectively). Sera from NOD mice bled on day 10 exhibited no detectable anti-idiotypic antibody binding to either c2B8 or lumiliximab regardless of whether or not animals were co-administered anti-mCD20 18B12 IgG2a (FIG. 5). Interestingly, the afucosyl hIgG1 Fc regions appeared to be more immunogenic than their wild type hIgG1 counterparts and generated anti-hIgG1 antibodies that were most likely not absorbed with 100 µg/ml CE9.1 hIgG1 (FIG. 5, rituximab aFuc and lumi aFuc). As found previously, each group of NOD mice treated with anti-mCD20 18B12 IgG2a generated a strong anti-idiotypic IgG response to the variable domain of 18B12 that was detected by a strong binding to 18B12 IgG1 (FIG. 5).

Example 4

Anti-Idiotypic Monoclonal Antibodies Generated from Anti-mCD20 IgG2a Immunized NOD Mice Recognize a Diversity of Epitopes and are of Different Isotypes Four hybridoma fusions to generate anti-idiotypic monoclonal antibodies to different target antigens were performed using splenocytes from IgG2a antigen and anti-mCD20 18B 12 IgG2a immunized NOD mice. Each fusion resulted in a panel of hybridomas producing monoclonal antibodies with a broad range of binding characteristics (summarized in Table 2). The fusion to generate anti-idiotypic antibodies to 18B12 anti-mCD20 was performed 8 days after a single i.p. administration of 18B12 IgG2a (100 μg in PBS). The strategy for generating anti-idiotypic antibodies to 2B8, C12 and M290 was to perform a primary immunization with antigen (IgG2a) co-administered with anti-mCD20 18B12 IgG2a (100 μg each in PBS i.p. for 2B8 IgG2a and M290 IgG2a antigens; 100 μg 18B12 IgG2a and 25 μg C12 IgG2a, each in PBS i.p.) followed by an i.p. boost 21 days later with antigen alone (100 μg 2B8 IgG2a or M290 IgG2a, respectively, in PBS) or 17 days later with antigen alone (C12 IgG2a, 50 μg in PBS). Fusions were performed 3 days after the boost. The M290 IgG2a fusion utilized spleen cells pooled from two seropositive mice and therefore generated more hybridomas (Table 2). Each fusion was screened for hybridomas producing IgG 1, IgG2b, or IgG2c antibodies that bound to all isotype variants available for the antigen but did not bind to a panel of isotype matched control antibodies.

TABLE 2

Diverse Anti-Idiotype Producing Hybridomas Generated from Anti-mCD20 18B12 IgG2a Immunized NOD Mice. Monoclonal antibodies produced by hybridomas from four independent fusions were predominantly IgG1/κ, with ~10% being IgG2b or IgG2c. Monoclonal antibodies were tested by flow cytometry for their ability to block their target antibody (anti-mCD20 18B12, anti-hCD20 2B8, anti-hBCMA C12 or anti-mCD103 M290) from binding antigen positive cells (mCD20 transfected 300.18, Ramos, H929 or C57B1/6 CD8$^+$ splenocytes, respectively). Antibodies showing ≥90% inhibition of antigen binding were scored, "+", those with 70% to 90% inhibition were scored "+/−", and those with ≤70% inhibition scored "−".

| Clone | Isotype | Blocks |
|---|---|---|
| Anti-18B12 (anti-mCD20) | | |
| 1 B6 | IgG2c κ | − |
| 4 E8 | IgG1 κ | + |
| 5 A7 | IgG1 κ | + |
| 5 F3 | IgG1 κ | + |
| 8 B6 | IgG2b κ | +/− |
| 15 F8 | IgG1 κ | +/− |
| 18 B7 | IgG1 κ | − |
| 18 B9 | IgG1 κ | − |
| 18 C8 | IgG2b κ | − |
| 18 E7 | IgG1 κ | + |
| 18 G12 | IgG1 κ | − |
| 18 H12 | IgG1 κ | +/− |
| 19 B3 | IgG1 κ | − |
| 21 D8 | IgG1 κ | − |
| 24 B1 | IgG1 κ | + |
| 26 A6 | IgG1 κ | + |
| 31 F10 | IgG1 κ | + |
| 32 C4 | IgG1 κ | + |
| 32 H1 | IgG1 κ | +/− |
| 35 B7 | IgG1 κ | + |
| 43 A2 | IgG1 κ | +/− |
| 45 E10 | IgG2c κ | − |
| 45 F8 | IgG1 κ | + |
| 50 F1 | IgG2b κ | + |
| Anti-2B8 (anti-hCD20) | | |
| 1 E2' | IgG1 κ | + |
| 1 H11 | IgG2b κ | + |
| 4 B5 | IgG1 κ | + |
| 5 G7 | IgG1 κ | + |
| 5 H10 | IgG1 κ | + |
| 7 H6 | IgG1 κ | − |
| 8 B2 | IgG1 κ | + |
| 8 H12 | IgG1 κ | + |
| 11 A11 | IgG1 κ | +/− |
| 11 E8' | IgG1 κ | + |
| 11 H9 | IgG1 κ | + |
| Anti-C12 (anti-BCMA) | | |
| 2 A11 | IgG1 κ | + |
| 2 C10 | IgG1 κ | + |
| 7 D10 | IgG1 κ | − |

Anti-M290 (anti-CD103)

| Clone | Isotype | Blocks | Clone | Isotype | Blocks |
|---|---|---|---|---|---|
| 1 D10 | IgG2b κ | + | 4 H3 | IgG1 | + |
| 2 C12 | IgG1 κ | + | 6 H1 | IgG1 | +/− |
| 3 B1 | IgG1 κ | + | 7 C11 | IgG1 | + |
| 3 C1 | IgG1 κ | + | 9 B9 | IgG1 | + |
| 4 F9 | IgG1 κ | + | 9 E11 | IgG1 | + |
| 5 E8 | IgG1 κ | + | 10 G2 | IgG1 | +/− |
| 6 B10 | IgG1 κ | + | 10 H12 | IgG1 | + |
| 8 B9 | IgG1 κ | + | 11 E6 | IgG1 | +/− |
| 8 G5 | IgG1 κ | +/− | 12 C5 | IgG1 | + |
| 9 H4 | IgG1 λ | +/− | 13 B8 | IgG1 | +/− |
| 10 A3 | IgG2b κ | +/− | 13 E5 | IgG1 | + |
| 10 C12 | IgG2b κ | + | 13 E7 | IgG1 | + |
| 10 E10 | IgG1 | + | 13 G2 | IgG1 | + |
| 11 A2 | IgG1 A | + | 13 H5 | IgG1 | − |
| 11 A8 | IgG1 | + | 14 A8 | IgG1 | +/− |
| 11 C5 | IgG1 κ | + | 14 C2 | IgG1 | + |
| 11 E2 | IgG1 κ | + | 14 D12 | IgG1 | + |
| 12 A10 | IgG2b κ | +/− | 15 B4 | IgG1 | + |
| 12 E12 | IgG1 κ | + | 15 G6 | IgG1 | − |
| 13 A10 | IgG1 κ | + | 15 H2 | IgG1 | + |
| 13 B11 | IgG2c κ | + | 16 F6 | IgG1 | +/− |
| 15 B6 | IgG1 κ | + | 17 D6 | IgG1 | + |
| 18 B3 | IgG1 | + | 18 A1 | IgG1 | − |
| 1 E1 | IgG1 | + | 18 C4 | IgG1 | + |
| 2 A6 | IgG1 | + | 18 D10 | IgG1 | + |
| 3 G11 | IgG1 | + | 19 A5 | IgG1 | + |
| 4 A7 | IgG1 | + | 19 C5 | IgG1 | + |
| 4 C3 | IgG1 | +/− | 19 D5 | IgG1 | + |

The dominant isotype produced by hybridomas from each fusion was IgG1, with approximately 10% of the hybridomas producing IgG2b or IgG2c (Table 2). The confirmed anti-idiotypic antibodies to anti-mCD20 18B12, rituximab 2B8, anti-hBCMA C12, and anti-mCD013 M290 were tested for their ability to block the binding of soluble target antibody to its antigen on cells (mCD20, hCD20, hBCMA or mCD103). An example of blocking and nonblocking anti-idiotypic antibodies to anti-mCD20 18B12 is shown in FIG. 6. One of the antibodies assayed produced by the 5A7 hybridoma, blocked binding of 18B12 to a mouse pre-B cell line (300.18) transfected with mouse CD20 (FIG. 6, open triangles). Anti-idiotypic antibodies of different isotypes were also assayed in cross-competition experiments to examine cross-blocking and epitope diversity. Anti-idiotypic monoclonal antibodies recognizing different epitopes and suitable for ELISA sandwich capture assays were found in each fusion. ELISA assays for quantification of 18B12 or M290 antibodies in mouse serum were developed and utilized for determining in vivo pharmacokinetics after dosing antibodies in animal disease models.

Example 5

Anti-Idiotype Antibodies can Bind Shared Epitopes on Highly Related Monoclonal Antibodies Whereas an antibody idiotype is generally defined by the differences in isotopes within the complementarity determining regions, similar or identical epitopes can still occur within the variable regions of distinct or related antibodies. In testing the panels of anti-idiotype antibodies for specificity to the immunizing antigen, it was demonstrated that the anti-idiotypic antibodies bind only to the immunogen IgG2a antibody or a class switched isotype with an identical variable domain, and not to a panel of antibodies of the same or different isotypes recognizing other antigens. The three anti-idiotype antibodies generated to anti-human BCMA C12 shown in Table 2 were also found to bind two highly related (by VH and VL amino acid sequences) anti-human BCMA antibodies (C11 and C13) (FIG. 7). The anti-human BCMA antibodies C11, C12, and C13 differ by only a few amino acids in their variable domains and bind overlapping epitopes on human BCMA. The anti-idiotype antibodies to C12 did not bind two other anti-human BCMA antibodies (A7 and Vicky-1) that bind non-overlapping and distinct epitopes on human BCMA. Furthermore, these three anti-idiotype antibodies to C12 did not bind a panel of anti-mouse BCMA antibodies, nor did they bind to anti-human CD20 2B8 or anti-mouse CD20 18B12 antibodies (FIG. 7).

In autoimmune diseases where the host breaks self-tolerance and generates a humoral response to a self antigen, the autoantibodies to a particular antigen may bind a single epitope or several limited epitopes. This lack of diversity in epitopes recognized by autoantibodies may allow anti-idiotype antibodies generated to one autoantibody to cross react with related autoantibodies targeting the same epitope. Therefore, anti-idiotype treatment for autoantibodies and diagnostic agents for autoantibodies have the potential to be more efficacious or broadly applicable than the "one anti-idiotype antibody to one autoantibody" paradigm would suggest.

Example 6

An Optimal Ratio of Anti-mCD20 IgG2a: Antigen IgG2a Results in a Higher Titer Anti-Idiotypic Humoral Response To optimize the anti-idiotype immunization protocol, the anti-mCD20 IgG2a: antigen IgG2a ratio was altered by increasing or decreasing the amounts of IgG2a antibodies used for immunization (listed in FIG. 8). The 2B8 IgG2a antibody was used as a test antigen since it was known to elicit an anti-idiotypic antibody response when co-administered with anti-mCD20 18B12 IgG2a (see FIG. 4). Immunizations done previously by administering a NOD mouse 100 μg anti-mCD20 18B12 IgG2a and 100 μg IgG2a antigen had resulted in relatively low but consistent primary anti-idiotypic IgG sera titer responses (titers of 500 to 3000; see FIGS. 3-5). Of the five different anti-mCD20 IgG2a: antigen IgG2a ratios tested in FIG. 8, a ratio different from that used previously, 100 μg anti-mCD20 18B12 IgG2a and 25 μg 2B8 IgG2a, resulted in the strongest primary anti-idiotype sera titer response to 2B8 IgG2a (FIG. 8). Increasing either antibody over these amounts resulted in a lower primary anti-idiotypic antibody response (FIG. 8).

Example 7

Anti-Idiotype Responses to Anti-Mouse CD20 18B12 IgG2a are Restricted to NOD-Related Mouse Strains Expressing the Igh-1$^b$ Allele of IgG2a Several mouse strains closely related to NOD were selected for immunization with anti-mCD20 18B12 IgG2a, 2B8 IgG2a, or both anti-mCD20 18B12 and 2B8 IgG2a antibodies to test whether the Igh-1 allele expressed in NOD mice and/or the antibody repertoire and immune system defects in NOD mice were critical for anti-idiotypic antibody generation. Mouse strains, their relevant phenotypes, and their ability to produce an anti-idiotypic antibody response are summarized in Table 3.

TABLE 3

Mouse Strains Tested for Anti-Idiotypic Antibody Responses. Mice (5 per group) were immunized with 2B8 IgG2a (100 μg, i.p. in PBS), anti-mCD20 18B12 IgG2a (100 μg, i.p. in PBS), or both anti-mCD20 18B12 IgG2a and 2B8 IgG2a (100 μg each, i.p. in PBS), bled on day 10, and sera assessed by ELISA for binding to 18B12 IgG1a, 2B8 IgG1a, or control IgG2a.

| Strain | Igh-1 Allotype | Geneology and Autoimmune Disease Susceptibility | 2B8 IgG2a Immunized: Anti-Idiotypic Antibody Response to 2B8* | 18B12 IgG2a Immunized: Anti-Idiotypic Antibody Response to 18B12* | 2B8 + 18B12 IgG2a Immunized: Anti-Idiotypic Antibody Response to 2B8* |
|---|---|---|---|---|---|
| NOD | Igh-1$^b$ | Derived from Swiss mice; older mice develop insulitis; unique MHC haplotype, defective APC and T cell regulation, defective NK cells and macrophages; lack complement C5 | − | +++ | ++ |
| NOR | Igh-1$^b$ | Insulitis resistant and diabetes free; elevated circulating T cells and defective peritoneal macrophage responses | − | +++ | ++ |
| SJL | Igh-1$^b$ | Susceptible to EAE; elevated circulating T cells; resistant to atherogenic diet | − | +++ | ++ |

TABLE 3-continued

Mouse Strains Tested for Anti-Idiotypic Antibody Responses. Mice (5 per group) were immunized with 2B8 IgG2a (100 μg, i.p. in PBS), anti-mCD20 18B12 IgG2a (100 μg, i.p. in PBS), or both anti-mCD20 18B12 IgG2a and 2B8 IgG2a (100 μg each, i.p. in PBS), bled on day 10, and sera assessed by ELISA for binding to 18B12 IgG1a, 2B8 IgG1a, or control IgG2a.

| Strain | Igh-1 Allotype | Geneology and Autoimmune Disease Susceptibility | 2B8 IgG2a Immunized: Anti-Idiotypic Antibody Response to 2B8* | 18B12 IgG2a Immunized: Anti-Idiotypic Antibody Response to 18B12* | 2B8 + 18B12 IgG2a Immunized: Anti-Idiotypic Antibody Response to 2B8* |
|---|---|---|---|---|---|
| SWR | Igh-1$^c$ | Derived from Swiss mice; susceptible to EAE, resistant to CIA due to TCR-V deletion/polymorphisms; genetically different from NOD | − | − | − |
| C.B-17 | Igh-1$^b$ | Congenic strain for Igh$^b$ H chain locus; derived from BALB/c × C57BL/Ka backcrossed to BALB/c | − | + | + |
| C57BL/6 | Igh-1$^b$ | When fed high fat diet, develop hyperinsulinemia; atherogenic diet induces atherosclerosis | − | + | + |
| BALB/C | Igh-1$^a$ | None | − | − | − |

*++, mean anti-idiotype titer >500 but <5,000; +, mean anti-idiotype titer >100 but <500; −, mean anti-idiotype titer <100. Mean titers of each group (NOR, SJL, and SWR only) are shown in FIG. 9.

The NOR mouse strain, most closely related to NOD (Serreze et al., 1994), generated a strong anti-idiotypic antibody response to 18B12 IgG2a alone and did not respond to the 2B8 IgG2a antibody in the absence of 18B12 IgG2a dosing (FIG. 9). SJL mice responded similarly to the NOR mouse strain. NOR and SJL mice dosed with both 18B12 IgG2a and 2B8 IgG2a generated an anti-idiotypic response to both antibodies, however the anti-idiotypic antibody titers to both antigens were lower than in mice of the same strains dosed with 18B12 IgG2a alone (FIG. 9). SWR mice made no detectable anti-idiotypic responses to any of the injected antibodies (FIG. 9). These studies are consistent with 18B12 IgG2a eliciting an anti-idiotypic response in autoimmune-prone mouse strains expressing the Igh-1$^b$ allotype.

Example 8

Use of Anti-Idiotypic Antibodies to Neutralize Anti-CD20 Antibodies

The anti-idiotypic antibodies generated in NOD mice treated with anti-mCD20 18B12 IgG2a have the unique ability to bind only the variable domain of the anti-mCD20 18B12 antibody. Of the anti-idiotypic antibodies that in vitro blocked binding of anti-mCD20 18B12 to mCD20 (Table 2, FIG. 6) three antibodies were selected to test for the ability to in vivo bind and functionally neutralize anti-mCD20 18B12 IgG2a. Mice were treated with a single dose of anti-mCD20 18B12 IgG2a and 7 days later administered an equal dose of anti-idiotype antibody (clones 4E8, 5A7, or 50F1). Levels of peripheral blood B cells and serum anti-mCD20 18B12 antibody were monitored after an additional 1, 3, and 7 days. All three anti-idiotype antibodies tested appeared to remove detectable anti-mCD20 18B12 from circulation within 24 hours of administration (data not shown). Seven days after treatment with the 4E8 anti-idiotype antibody mice minimally demonstrated B cell return that was not significantly different from animals not treated with anti-idiotype antibodies. Mice treated with either the 5A7 and 50F1 anti-idiotype antibodies (both IgG1/κ) demonstrated strong repopulation of B cells 7 days after anti-idiotype treatment. B cell repopulation was highest in mice after administration of the 5A7 anti-idiotype antibody, and a time course of B cell repopulation was subsequently performed with this anti-idiotype antibody (FIG. 10). Systemic B cell repopulation was initiated and was evident by one day after administration of the 5A7 anti-idiotype antibody (FIG. 10). CD19$^+$ B cells in the blood reached 60% of normal levels within 1 week after the 5A7 anti-idiotype antibody was administered, while anti-mCD20 18B12 treated mice that had not received the 5A7 antibody remained B-cell depleted (FIG. 10). No adverse effects on mouse health were seen after administration of the 5A7 anti-idiotype antibody and resulting neutralization of anti-mCD20 antibody.

Example 9

Cell-Based Anti-CD20 Antibody Immunization of NOD Mice

To determine if any cell-bound IgG2a would induce an anti-idiotypic antibody response and if B cells were required for anti-idiotypic antibody generation, splenocytes (T and B cells) and thymocytes (immature T cells; CD20) were coated ex-vivo with 18B12 IgG2a or anti-H-2 Db IgG2a (clone 27-11-13S), washed, and injected i.p. into NOD mice with or without soluble 2B8 IgG2a. Sera were collected on day 10 and tested for anti-idiotypic IgG responses to 2B8 or 18B12. Anti-mCD20 18B12 IgG2a could induce an anti-idiotypic antibody response when pre-coated on splenocytes (B cells) or dosed soluble in PBS without cells or with thymocytes (FIG. 11A). Anti-H-2D$^b$ IgG2a treated mice generated a mild anti-IgG2a isotype response and only when anti-H-2D$^b$ IgG2a was dosed with splenocytes, whereas 2B8 IgG2a treated mice did not generate any antibody response. No anti-idiotypic antibodies to 2B8 IgG2a were found in mice additionally dosed with anti-H-2D$^b$ IgG2a (FIG. 11A). It appeared that the soluble antigen 2B8 IgG2a decreased the low level of anti-idiotypic antibody generation by splenocyte-bound 18B 12 IgG2a. This was likely due to the ratio of the injected antibodies being less than optimal (in this case ~20 µg 18B12 IgG2a and 50 µg 2B8 IgG2a) with an excess of 2B8 IgG2a competing with the 18B12 IgG2a.

To test whether the finding in FIG. 11A, that mouse B cells pre-coated with anti-mouse CD20 18B12 IgG2a could be used to immunize NOD mice and generate an anti-idiotypic antibody response to anti-mouse CD20 18B12, could be extended to human B cells pre-coated with anti-human CD20 2B8 IgG2a, the human SKW6.4 Burkitt's lymphoma cell line was pre-coated with anti-human CD20 2B8 IgG2a, washed, and injected into NOD mice. Pre-coated cells were injected alone or with the addition of soluble anti-mouse CD20 18B12 IgG2a or anti-mouse CD103 M290 IgG2a. An anti-idiotypic response to anti-mouse CD20 18B12 IgG2a was generated whenever 18B12 IgG2a was used to immunize NOD mice, however an anti-idiotypic response to the anti-human CD20 2B8 IgG2a antibody was not generated when this antibody was coated on human B lymphoma cells, even in the presence of soluble anti-mouse CD20 18B12 IgG2a (FIG. 11B). This suggests that the co-administered antigen IgG2a to which it is desired to generate an anti-idiotypic antibody response is required to be soluble and not cell bound. In this example anti-CD103 M290 IgG2a was also used as a co-administered IgG2a antibody with human B lymphoma cell-bound 2B8 IgG2a. No anti-idiotypic antibody responses were generated to 2B8 IgG2a or M290 IgG2a, however in this antigen combination the M290 IgG2a elicited a measurable anti-IgG2a isotype specific response (FIG. 11B), similar to what was previously found using anti-H-2 Db IgG2a bound to splenocytes as an antigen (FIG. 1A).

What is claimed is:

1. A method for producing anti-idiotypic antibodies comprising:
   (a) co-administering to a mouse a first antibody having a murine IgG2a isotype and a second antibody that targets mouse B cells and has a murine IgG2a isotype; wherein the first and second antibodies have different binding specificities, wherein the first antibody is soluble, wherein the mouse expresses the Igh-1$^b$ allele of IgG2a, and wherein the second antibody binds a mouse B cell surface marker selected from the group consisting of CD19, CD20, CD21, CD22, CD40, CD45, IgM, and IgD;
   (b) producing a hybridoma fusion of spleen cells from the immunized mouse and myeloma fusion partners; and
   (c) isolating the anti-idiotypic antibodies which specifically bind to the first antibody in step (a).

2. The method of claim 1, wherein said mouse is susceptible to autoimmune disease.

3. The method of claim 1, wherein the myeloma fusion partners are either NS-1 or SP2/0 cells.

4. The method of claim 1, wherein said mouse is selected from the group consisting of: non-obese diabetic (NOD), non-obese resistant (NOR), SJL, C.B-17, and C57BL/6.

5. The method of claim 4, wherein said mouse is a NOD mouse.

6. The method of claim 1, wherein said co-administration is performed sequentially.

7. The method of claim 6, wherein the sequential co-administrations are given as boosting administrations.

8. The method of claim 1, wherein said co-administration is performed simultaneously.

9. The method of claim 1, wherein said first and second antibody are administered at a ratio of about 1:1.

10. The method of claim 1, wherein said first and second antibody are administered at a ratio of about 1:2.

11. The method of claim 1, wherein said first and second antibody are administered at a ratio of about 1:4.

12. The method of claim 1, wherein said second antibody is the anti-mCD20 antibody 18B 12.

13. The method of claim 1, wherein said first antibody specifically binds an antigen selected from the group consisting of: alpha-4-integrin, glycoprotein I1b/I11a, vascular endothelial growth factor, epidermal growth factor, complement C5 protein, ErbB2, CD3 receptor, CD11a, CD20, CD23, CD25, CD33, CD52, BCMA, CD40, Lymphotoxin α, Lymphotoxin $α_1β_2$, LIGHT, TWEAK, CD154, VLA4, EGFR, IGF1R, CD169, IL-6, IL-23, TNF-α, Neonatal Fc Receptor (FcRn), BDCA-2, DCIR, DR6 (Death Receptor 6), LINGO-I, Tyro3, RON receptor tyrosine kinase, DDR1 (Discoidin Domain Receptor 1), HER3, FN14, VEGF and CD103.

14. The method of claim 13, wherein said first antibody comprises the variable domains of rituximab.

15. A method for producing anti-idiotypic antibodies comprising:
   (a) co-administering to a mouse a first antibody having a murine IgG2a isotype and a second antibody that targets the mouse B cell surface marker CD20 and has a murine IgG2a isotype, wherein the first and second antibodies have different binding specificities, wherein the first antibody is soluble, wherein the mouse expresses the Igh-1 b allele of IgG2a;
   (b) producing a hybridoma fusion of spleen cells from the immunized mouse and myeloma fusion partners; and
   (c) isolating the anti-idiotypic antibodies which specifically bind to the first antibody in step (a).

16. The method of claim 15, wherein said mouse is susceptible to autoimmune disease.

17. The method of claim 15, wherein the myeloma fusion partners are either NS-1 or SP2/0 cells.

18. The method of claim 15, wherein said mouse is selected from the group consisting of: non-obese diabetic (NOD), non-obese resistant (NOR), SJL, C.B-17, and C57BL/6.

19. The method of claim 15, wherein said mouse is a NOD mouse.

20. The method of claim 15, wherein said co-administration is performed sequentially.

21. The method of claim 20, wherein the sequential co-administrations are given as boosting administrations.

22. The method of claim 15, wherein said co-administration is performed simultaneously.

23. The method of claim 15, wherein said first and second antibody are administered at a ratio of about 1:1, about 1:2, or about 1:4.

24. The method of claim 15, wherein said first antibody specifically binds an antigen selected from the group consisting of: alpha-4-integrin, glycoprotein I1b/I11a, vascular endothelial growth factor, epidermal growth factor, complement CS protein, ErbB2, CD3 receptor, CD11a, CD20, CD23, CD25, CD33, CD52, BCMA, CD40, Lymphotoxin α, Lymphotoxin $α^1β^2$, LIGHT, TWEAK, CD I 54, VLA4, EGFR, IGFI R, CD169, IL-6, IL-23, TNF-α, Neonatal Fc Receptor (FcRn), BDCA-2, DCIR, DR6 (Death Receptor 6), LINGO-I, Tyro3, RON receptor tyrosine kinase, DDR1 (Discoidin Domain Receptor 1), HER3, FN14, VEGF and CD103.

25. The method of claim 24, wherein said first antibody comprises the variable domains of rituximab.

* * * * *